United States Patent [19]

Roederer

[11] Patent Number: 5,714,386
[45] Date of Patent: Feb. 3, 1998

[54] CY7-ALLOPHYCOCYANIN CONJUGATES FOR USE IN MULTIPLEX FLUORESCENCE DETECTION ASSAYS

[75] Inventor: Mario Roederer, Redwood City, Calif.

[73] Assignee: Board of Trustees of the Leland Stanford Junior University, Palo Alto, Calif.

[21] Appl. No.: 585,302

[22] Filed: Jan. 11, 1996

[51] Int. Cl.[6] .................. G01N 33/533; G01N 33/554; C07K 17/02
[52] U.S. Cl. .................. 436/546; 435/6; 435/7.21; 435/7.24; 436/520; 436/536; 436/800; 530/370; 530/391.3; 530/391.5; 530/395; 530/408; 530/409; 530/807
[58] Field of Search .................. 435/7.21, 7.24, 435/6; 436/519, 520, 521, 800, 546, 536; 530/807, 391.3, 391.5, 370, 395, 408, 409

[56] References Cited

U.S. PATENT DOCUMENTS

| | | | |
|---|---|---|---|
| 4,542,104 | 9/1985 | Stryer et al. | 436/536 |
| 4,666,862 | 5/1987 | Chan | 436/501 |
| 5,268,486 | 12/1993 | Waggoner et al. | 548/455 |
| 5,272,257 | 12/1993 | Gupta | 436/501 |

OTHER PUBLICATIONS

Mujumdar et al., "Cyanine Dye Labeling Reagents: Sulfoindocyanine Succinimidyl Esters," Bioconjugate Chemistry (1993), 4:105–111.

Southwick et al., "Cyanine Dye Labeling Reagents—Carboxymethylindocyanine succinimidyl Esters[1]," Cytometry (1990), 11:418–430.

Ernst et al., "Cyanine Dye Labeling Reagents for Sulfhydryl Groups[1]," Cytometry (1989), 10:3–10.

Mujumdar et al., "Cyanine Dye Labeling Reagents Containing Isothiocyanate Groups[1]," Cytometry (1989), 10:11–19.

Lansdorp et al., "Single Laser Three Color Immunofluorescence Staining Procedures Based on Energy Transfer Between Phycoerythrin and Cyanine 5[1]," Cytometry (1991), 12:723–730.

M. Roederer et al., Cytometry, vol. 24, pp. 191–197, 1996.

A. Beavis et al., Cytometry, vol. 24, pp. 390–394, 1996.

*Primary Examiner*—Mary E. Ceperley
*Attorney, Agent, or Firm*—Flehr Hobach Test Albritton & Herbert LLP

[57] ABSTRACT

Novel tandem dyes comprising a conjugate of a Cy7 dye and allophycocyanin are provided. Also provided are probes comprising the subject dyes conjugated to a member of a specific binding pair. Probes comprising the subject tandem dyes find use as labels in variety of fluorescence detection assays.

20 Claims, 3 Drawing Sheets

CY7-ALLOPHYCOCYANIN CONJUGATES FOR USE IN MULTIPLEX FLUORESCENCE DETECTION ASSAYS

ACKNOWLEDGMENT OF GOVERNMENT RIGHTS

This invention was made with Government support under contract no. CA42509 awarded by the National Institutes of Health. The Government has certain rights in this invention.

INTRODUCTION

1. Field of the Invention

The field of this invention is fluorescent labels for use in biological detection applications

2. Background

Although many different types of labels have found use in biological detection assays, of increasing interest are fluorescent labels. Fluorescence labels or dyes have found use in many applications, including cell sorting, diagnostic assays, histology, fluorescence microscopy, immunocytochemical localization of antigenic markers, e.g. for pathogens, and the like. The use of fluorescent labels with antibodies, DNA probes, biochemical analogs, lipids, drugs, cytokines, cells and polymers has expanded rapidly in recent years due to both improvements in detection instrumentation, such as electronic imaging microscopes and flow cytometers, and the increased number of new fluorescent labeling reagents.

The particular fluorescent label employed plays an important part in the sensitivity and accuracy of any particular methodology. In many situations, the sample which is involved has endogenous fluorescence or autofluorescence which can provide for a substantial background. Other errors can be introduced through Rayleigh and Raman scattering. Many of these problems have been attempted to be addressed by having large Stokes shifts and emission at long wavelengths. In this situation, the excitation light which is employed is at substantially shorter wavelengths from the emission light, so that the background light may be filtered out. Thus, fluorescent labels which have high quantum efficiencies, so as to provide for intense signals, and emit at longer wavelengths so as to avoid the background signal resulting from background light are of particular interest.

Despite the large number of fluorescent labels that have been developed, further progress in assays employing fluorescent labels requires the development of new fluorescent labels which satisfy one or more of the following criteria: increased fluorescence brightness, improved photostability, lower non-specific binding, and excitation and emission wavelengths better matched to instrumentation light sources and detectors. Thus, there is continued interest in the development of new fluorescent dyes which are capable of satisfying one or more of the above criteria.

Relevant Literature

U.S. Patents describing phycobiliproteins and their use as fluorescent labels in biological assays include U.S. Pat. No. 4,520,110 and 4,542,104.

Properties of phycobiliproteins are described by Oi et al., *J. Cell Biol.* (1982), 93:981–986. Characteristics of phycobiliproteins may be found in Glazer and Hisxon, *J. Biol. Chem.* (1977), 252:32–42 and Grabowski & Gantt, *Photochem. Photobiol.* (1978), 28:39–45. See also Lundell & Glazer, *J. Biol. Chem.* (1981), 256:12600–12606. Other references of interest are: Glazer, 1981, in *The Biochemistry of Plants*, (Hatch and Boardman, eds., Academic Press, New York), 8:51–96; Bryant et al., *Arch. Microbiol.* (1976), 110:61–75 and Stryer, Ann. Rev. Biochem. (1978) 47:819–846.

Cyanine dyes are described in U.S. Pat. Nos.: 5,268,486; 4,337,063; 4,404,289; 4,405,711, as well as EP 1,529,202. Cyanine dye derivatives are also described in: Mujumdar et al., "Cyanine Dye Labeling Reagents: Sulfoindocyanine Succimidyl Esters," Bioconj. Chem. (1993) 4:105–111; Southwick et at., "Cyanine Dye Labeling Reagents— Carboxymethylindocyanine Succinimidyl Esters," Cytometry (1990) 11:418–430; Ernst et al., "Cyanine Dye Labeling Reagents for Sulfhydryl Groups," Cytometry (1989) 10: 3–10; Mujumdar et at., "Cyanine Dye Labeling Reagents Containing Isothiocyanate Groups," Cytometry (1989) 10: I 1–19.

The preparation and labeling properties of conjugate labels comprising an immune complex of PE and Cy5-anti-PE is reported in Lansdorp et al., "Single Laser Three Color Immunofluorescence Staining Procedures Based on Energy Transfer Between Phycoerythrin and Cyanine 5," Cytometry ( 1991 ) 12:723–730.

SUMMARY OF THE INVENTION

Tandem fluorescent dyes comprising a conjugate of a Cy7 dye and allophycocyanin are provided. Also provided are probes comprising the subject tandem dyes conjugated with a member of a specific binding pair. The probes find use as labels in a variety of fluorescence detection assays, including multiplex assays in which a plurality of fluorescent labels are employed.

DESCRIPTION OF THE SPECIFIC EMBODIMENTS

Figure 1A:
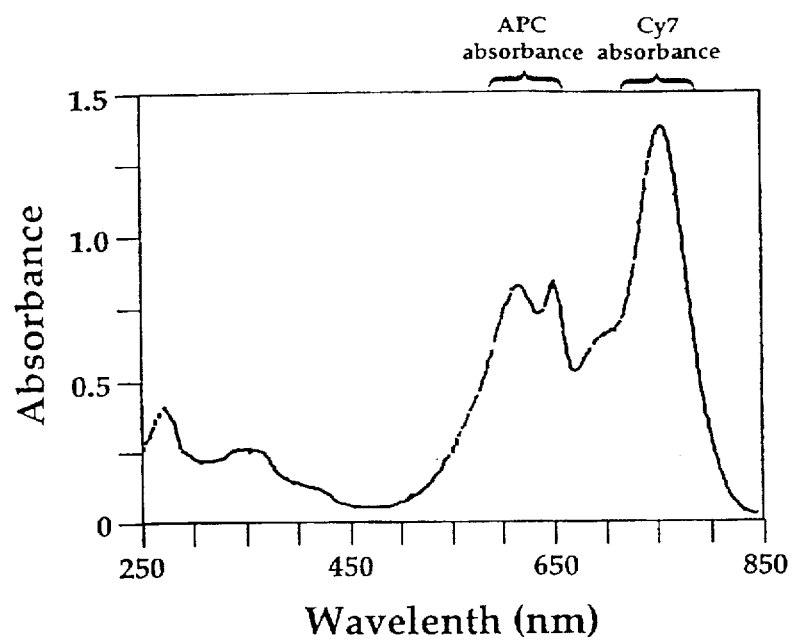
FIG. 1A provides the absorbance spectrum for a Cy-7-APC tandem dye according to the subject invention.

Novel tandem fluorescent dyes comprising a conjugate of a Cy7 dye and allophycocyanin are provided. Also provided are probes comprising the subject tandem dyes conjugated to a member of a specific binding pair. Probes comprising the subject tandem dyes find use in a variety of fluorescence detection based assays.

In the subject tandem dye conjugates, one or more Cy7 moieties are bound to an allophycocyanin moiety in energy transfer relationship. The number ratio of Cy7 moieties to the allophycocyanin moiety in the subject dyes will generally range from 1 to 20, usually from 2 to 10, more usually from 3 to 8. By energy transfer relationship is meant that at least about 20% of the energy absorbed by the allophycocyanin is transferred to the bound Cy7 moieties, with usually at least about 50% of the energy, and more usually at least about 60% of the energy being transferred to the bound Cy7 moieties. The distance between each Cy7 moiety and the allophycocyanin moiety will generally range from about 3 to 15 nm, usually between about 3 to 10 nm, more usually between 4 to 8 nm.

The Cy7 dyes of subject conjugates are cyanine dyes having seven carbon atom polymethine bridges, where these dyes individually have sharp, intense absorption bands and a sharp emission profiles, with Stokes shifts ranging from between 10 and 30 nm, usually from between 10 and 25 nm, more usually from between 15 and 25 nm. The extinction coefficient of the Cy7 dyes will exceed at least about 50,000 cm$^{-1}$ M$^{-1}$ usually at least about 100,000cm$^{-1}$M$^{-1}$, and may be as high as 250,000 cm$^{-1}$M$^{-1}$, or higher. The quantum yield will generally range from 0.1 to 1.0, more usually from 0.1 to 0.6. The absorption maximum of the Cy7 dyes will range from 700 to 770 nm, usually from 720 to 760 nm, more usually from 740 to 760 nm, and the emission maximum will range from 760 to 800 nm, usually from 770 to 790 nm, more usually from 775 to 785 nm.

The Cy7 dyes will have a molecular weight ranging from 350 to 1200 dal, usually from 400 to 1000 dal, and more usually from 500 to 1000 dal, depending on the various functional groups covalently bonded to the cyanine moiety. The Cy7 dyes will have at least one, usually one, reactive functional group which may serve in the covalent bonding of the Cy7 and allophycocyanin moieties. Reactive functional groups will usually be amine reactive groups such as succinimidyl ester, isothiocyanate and the like, although other reactive functional groups may be employed, especially where reactive functional groups are introduced onto the allophycocyanin moiety or cross-linking reagents are employed in conjugation, as described below. To enhance the water solubility of the cyanine, water solubility enhancing functional groups may also be incorporated into the structure of the cyanine fluorescers, which groups include polar and ionic groups, such as hydroxy, sulfonate, sulfate, carboxylate, substituted amino, and quaternary groups.

Cy7 dyes suitable for use in the subject conjugates may be described by the formula:

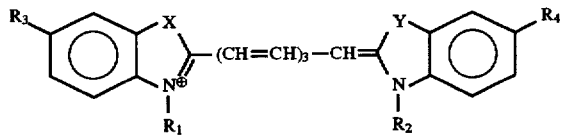

wherein X and Y are the same or different and may be heteroatoms, usually O or S, or alternatively one or both of X and Y may be isopropylidene; and R1 to R4 we the same or different and are selected from: (a) reactive functional groups which provide for covalent bonding to the allophycocyanin; water solubility enhancing groups and (c) lower alkyls of 1 to 6 carbon atoms, usually 1 to 4 carbon atoms, where the alkyl may be straight chained or branched. Substituents on the ring which may serve as reactive functional groups include groups comprising moieties selected from isothiocyanate, isocyanate, monochlorotriazine, dichlorotriazine, dichlorotriazinylamine, mono-or di-halogen substituted pyridine, maleimide, aziridine, sulfonyl halide, acid halide, hydroxysuccinimide ester, hydroxysulfosuccinimide ester, imido ester, hydrazinyl, azidonitrophenyl, azide, 3-(2-pyridyl dithio)-propionamide, amino, iodoacetamide, iodoacetamidomethyl, and the like. Specific water solubility enhancing groups include alkyl sulfonates, where the alkyl group ranges from 2 to 4 carbon morns in length. See U.S. Pat. No. 5,268,486, the disclosure of which heroin incorporated by reference.

Specific Cy7 dyes of interest include Cy7.4-IA, Cy7.8-ITC, Cy7.11-OH, Cy7.12-OH, Cy7.13-OR, and the like. Specific Cy7 dyes comprising water solubility enhancing groups include Cy7.18-OH, and the like. (The above names in accordance with the nomenclature proposed by the literature for cyanine dyes, wherein the formula Cy7.#ZZ, Cy7 designates that the dye is a cyanine dye having 7 carbon atoms in its polymethine bridge, # is a unique number assigned to the specific Cy7 compound which is based on the specific R1, R2, X and Y groups of the compound and ZZ is the reactive functional group present on the dye. See Mujumdar et al., "Cyanine Dye Labeling Reagents: Sulfoindocyanine Succimidyl Esters," Bioconj. Chem. (1993) 4:105–111, as well as the other cyanine dye references listed under Relevant Literature, supra).

The Cy7 dyes suitable for use as in the subject dyes may be purchased commercially or readily synthesized, using procedures known in the literature (See Relevant Literature, supra).

As mentioned above, in the subject tandem dye conjugates, at least one Cy7 dye moiety, where the particular moiety is usually the same when a plurality are present, will be bound to allophycocyanin (APC), where the properties of allophycocyanin are described in U.S. Pat. No. 4,520,110, the disclosure of which is herein incorporated by reference.

In preparing the subject tandem dye conjugates, the Cy7 and allophycocyanin moieties may be conjugated through any convenient means. Thus, conjugation may be achieved through covalent bonding or coupling of functionalities present on the Cy7 moiety and allophycocyanin, e.g. a Cy7 comprising an amine reactive functional group such as succinimidyl ester may react with an amine of available lysine residues of the allophycocyanin to form a covalent bond between the two moieties. Alternatively, monofunctional groups may be introduced onto one or both of the Cy7 and allophycocyanin moieties which provide for covalent bonding, e.g. where the Cy7 comprises a thiol reactive group, a maleimido group may be introduced onto the allophycocyanin. In addition, bifunctional cross-linking reagents may be employed, where the bifunctional cross-linking reagents may be homo-or heterobifunctional, with heterobifunctional reagents being preferred.

Probes useful in fluorescent detection assays may be prepared by conjugation of the subject tandem dyes to a member of a specific binding pair, said pair consisting of ligands, receptors, nucleic acids, and the like. Conjugation may be through either non-covalent or covalent bonding, usually covalent bonding of the allophycocyanin moiety to the specific binding pair member.

Depending upon the nature of the specific binding pair member to be conjugated, the ratio of the two moieties will vary widely, where there may be a plurality of tandem dyes to one specific binding pair member or a plurality of specific binding pair members to one dye conjugate. For small molecules, that is, of molecular weight less than 2 kDal, there will generally be on the average at least one and not more than about 100, usually not more than about 60 conjugated to a dye. With larger molecules of at least about 2 kDal, the ratio of dyes to ligand or receptor may vary widely, since a plurality of dyes may be present in the conjugate or a plurality of the specific binding pair members may be present in the conjugate. In addition, in some instances, complexes may be formed by covalently conjugating a small ligand to the allophycocyanin of the dye and then forming a specific binding pair complex with the complementary receptor, where the receptor may then serve as a ligand or receptor in a subsequent complex, e.g. biotin and avidin.

Where the specific binding pair member is a ligand, the ligand may be any compound of interest for which there is a complementary receptor. For the most part, the ligands of interest will be compounds having physiological activity, either naturally occurring or synthetic. One group of compounds will have molecular weights in the range of about 125 to 2,000 d, snore usually from about 125 to 1,000 d, and will include a wide variety of drugs, oligopeptides, oligonucleotides, vitamins, enzyme substrates, coenzymes, pesticides, hormones, lipids, etc. These compounds for the most part will have at least one heteroatom, normally chalcogen (oxygen or sulfur) or nitrogen and may be aliphatic, alicyclic, aromatic, or heterocyclic or combinations thereof. Illustrative compounds include epinephrine, prostaglandins, thyroxine, estrogen, corticosterone, ecdysone, digitoxin, aspirin, penicillin, hydrochlorothiazide, quinidine, oxytocin, somatostatin, diphenylhydantoin, retinol, vitamin K, cobalamin, biotin and folate, to name just a few.

Compounds of greater molecular weight, generally being 2 kDal or more molecular weight, include poly(amino acids)-polypeptides and proteins-polysaccharides, nucleic acids, and combinations thereof e.g. glycosaminoglycans, glycoproteins, ribosomes, etc. Illustrative compounds include albumins, globulins, hemoglobin, surface proteins on cells, such as T- and B-cells e.g. Thy, Ia, tumor specific antigens, α-fetoprotein, retinol binding protein, C-reactive protein, enzymes, toxins, such as cholera toxin, diphtheria toxin, botulinus toxin, snake venom toxins, tetrodotoxin, saxitoxin, lectins, such as concanavalin, wheat germ agglutinin, and soy bean agglutinin, immunoglobulins, complement factors, lymphokines, mucoproteins, polysialic acids, chitin, collagen, keratin, etc.

For conjugation through covalent bonding of the allophycocyanin to the specific binding pair member, any convenient method may be employed, where a variety of methods are known and reported in the literature. See U.S. Pat. No. 5,520,110, as well as A. N. Glazer, *The Proteins*, Vol. IIA, 3rd ed., N. Neurath and R. L. Hill, eds., Academic Press, pp. 1–103 (1976); A. N. Glazer et al., "Chemical Modification of Proteins", *Laboratory Techniques in Biochemistry and Molecular Biology*, Vol. 4, PRT I, T. S. Work and E. Work, eds., North-Holland Publishing Co. (1975); and K. Peters et al., *Ann. Rev. Biochem.*, 46, 423–51 (1977), the descriptions of which are incorporated herein by reference. Thus, depending on the specific functional groups available on the specific binding pair member and tandem dye moieties, covalent bonding may occur upon direct reaction of monofunctional groups present on these moieties or a monofunctional group may be introduced onto one or both of these moieties which provides for covalent coupling. Alternatively, crosslinking agents may be employed, where these agents are homo or heterobifunctional agents, as described above. Examples of commercially available crosslinking reagents, as well as reagents available for introducing monofunctional groups onto proteins, are disclosed in the Handbook of Fluorescent Probes and Research Chemicals, Molecular Probes, Eugene, OR, 1992, pp 54–61.

As previously indicated, instead of having a covalent bond between the specific binding pair member of interest and the allophycocyanin moiety of the tandem dye, non-covalent bonds may be employed. For example, if one wishes to conjugate the tandem dye to avidin, biotin may be covalently conjugated to the allophycocyanin, and the resulting biotinylated allophycocyanin combined with avidin, whereby a tandem dye labeled avidin will result.

The subject tandem dyes which provide for a bright signal in the 760 to 800 nm range, where the quantum yield or fluorescence efficiency of the dye may range from 0.05 to 1.0, usually from 0.1 to 0.5, may be used in a wide variety of ways, enhancing known methodologies for the detection, diagnosis, measurement and study of antigens, either present as individual molecules, or in more complex organizations, such as viruses, cells, tissue, organelles e.g. plastids, nuclei, etc.

One of the uses of the subject probes is in fluorescent staining of cells. The cells may then be observed under a microscope, the presence of the tandem dye label being diagnostic of the presence of a specific determinant site or the cells may be used in a fluorescence activated cell sorter (FACS). Another use of the subject probes is in immunoassays or competitive protein binding assays, where the subject probes serve as fluorescent labels. Here, the allophycocyanin of the tandem dye may be conjugated to either a ligand or a receptor, particularly an antibody. While for the most part the antibodies will be IgG, other antibodies such as IgA, IgD, IgE and IgM may also find use. In addition, various naturally occurring receptors may be employed, particularly receptors having high binding specificity, such as avidin. By biotinylating either the specific binding pair member, the tandem dye or both, one can link various molecules through avidin. A wide variety of fluorescent assays are known. A few of these assays are illustrated in U.S. Pat. Nos. 3,998,943; 3,985,867; 3,996,345; 4,036,946; 4,067,959; 4,160,016 and 4,166,105, the relevant portions of which are incorporated herein by reference.

Of particular interest is the use of probes comprising the subject tandem dyes in multiplex assays, where a plurality of fluorescent labels are employed. In multiplex assays employing the probes comprising the subject tandem dyes, at least one of the labels will share a common excitation spectrum with the subject tandem dye, where the common excitation spectrum will range from about 600 to 680 nm, usually from about 600 to 660 nm. The total number of different labels employed, where one of the labels is the subject tandem dye, will be at least two, usually at least three, and may be ten or more, but will usually not exceed ten, and more usually not exceed eight. The emission maximum of each of the labels employed in the multiplex assay should differ by at least about 15 nm, usually at least about 25 nm. Other fluorescent labels that may be employed with the subject tandem dyes in multiplex assays include cyanine dyes, e.g. Cy3 and Cy5 dyes and conjugates thereof, e.g. Cy5-PE; phycobillins and conjugates thereof, e.g. phycoerythrin, phycocyanin, allophycocyanin; TEXAS RED®; CASCADE BLUE®, fluorescein, dansyl, umbelliferone, benzoxadiazoles, pyrenes, rose bengal, and the like.

By using combinations of fluorescers, one can provide for the detection of subsets of aggregations, such as particular types of cells, strains of organisms, strains of viruses, the natural complexing or interaction of different proteins or antigens, etc.

Conveniently, kits comprising the subject tandem dyes are provided, where the subject tandem dyes are present in combination with a plurality of fluorescent labels each having unique spectral characteristics. Usually the subject tandem dye will be present in combination with 1 to 10 additional fluorescent labels, usually 2 to 8 additional fluorescent labels, more usually 2 to 6 additional fluorescent labels, where at least one of the fluorescent labels will share a common excitation spectrum with the subject tandem dye.

The following examples are offered by way of illustration and not by way of limitation:

EXPERIMENTAL

1. Preparation of Cy7-APC Conjugate
   A. Materials:
   Reaction Buffer:
   500 mM carbonate ($Na_2CO_3$, 106g/mole, 1.7g $NaHCO_3$, 84g/mole, 2.8g per 100 ml) pH 9.5. No Azide.
   Reagents:

Cy7 succinimidyl ester, reactive dye (Cy7.18-OSU or Cy7obis-OSU (Biological detection systems)) See Mujumdar et al., Biochemistry Conj. supra.

APC:

Purified allophycocyanin (Molecular Probes, A-803). APC purity was checked by measuring the absorbance at 280, 620 and 655 nm.( 1 mg/ml of APC has an OD at 655nm of 5.9). A 655/620 ratio>1.4 indicates adequate removal of PC; a 655/280 ratio>4 indicates adequate removal of all other proteins.

B. Methods:

APC was equilibrated into the reaction buffer by gel filtration (e.g. PD-10, 9 ml column, Pharmacia). The APC concentration was calculated from the absorbance spectrum of the APC. 10 mg of reactive Cy7 succinimidyl ester derivative were dissolved in 1 ml anhydrous DMSO. The dissolved Cy7 was combined immediately with the APC to give a molar ratio of Cy7 to APC of 4–20. The resultant mixture was incubated and rotated at room temperature for 2 hours.

The Cy7-APC conjugate was removed by gel filtration and exchanged into PBP buffer (50 mM sodium phosphate, pH 7.0, 1 mM EDTA).The F/P and Protein concentration were determined by measuring the absorbance at 756 and 651.

The resulting tandem dye had an absorbance spectrum reflecting the presence of both the APC as well as the Cy7 dye (see FIG. 1A). The tandem dye shows the typical bimodal APC absorption band centered between 600 and 650 nm. Unmodified APC has little or no absorption above 700 nm. The tandem, on the other hand, shows a strong absorption band at 760 nm, which is typical for Cy7.

Figure 1B:
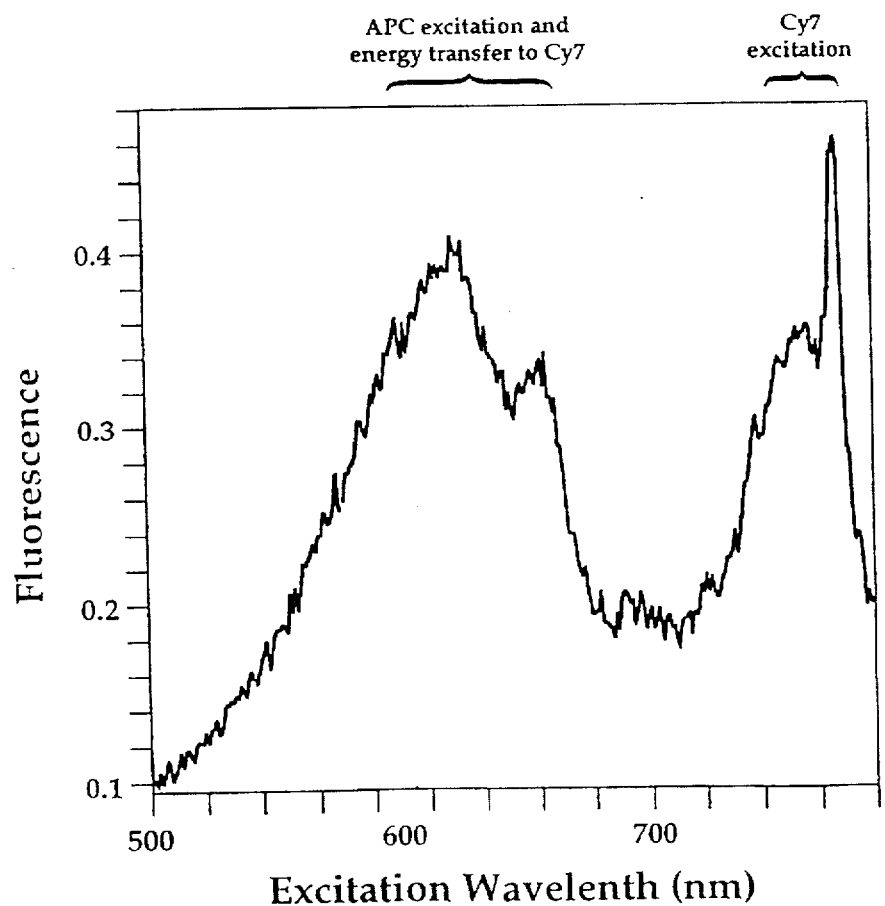
FIG. 1B provides the fluorescence spectrum for a Cy-7-APC tandem dye according to the subject invention.

The tandem also has a fluorescence emission spectrum that has characteristics of both APC as well as Cy7 emissions (FIG. 1B). The APC emission was quenched 80% in the tandem dye compared to unconjugated APC-i.e., by the presence of Cy7. In addition, the tandem shows a 780 emission band that is unique to Cy7. This emission band can be seen with 600 nm excitation, unlike that for unconjugated Cy7. It was concluded that this emission could only result from resonance energy transfer between the conjugated Cy7 and APC molecules.

2. Preparation of Cy7-APC-CD45RA Conjugate

Cy7-APC conjugate as prepared in Example 1 was coupled to CD45RA using protein-protein conjugation chemistry as follows:

First, free amino groups on the APC were reacted with SMCC to yield a maleimide-labeled APC. To produce the maleimide labeled conjugate, Cy7-APC from example 1 was dialyzed or exchanged into PBP buffer in amount sufficient to provide 1.7 mg of Cy7-APC per mg of IgG to be modified (this amount includes an extra 10% for loss during buffer exchanges). A 10 mg/ml stock solution of SMCC (succinimidyl 4-(N-maleimidomethyl)cyclohexane-1-carboxylate, Pierce No. 22320, NW334.3) in dry DMSO was prepared immediately following preparation of the SMCC stock solution, the SMCC stock solution was combined with Cy7-APC at a rate of 6μl per mg while vortexing. The reaction tube was wrapped in aluminum foil and rotated at room temperature for 60 minutes.

Next, IgG specific for CD45RA (obtained from PharMingen, San Diego) was prepared by reducing the hinge disulfide bonds to yield free sulfhydryls. First, a fresh solution of 1M dithiothreitol (DTT, MW 154.2, 15.4 mg/100 μl) in distilled water was prepared. A 4 mg/ml IgG solution in MES buffer (50 mM 2-N-[morpholino]ethanesulfonic acid, pH 6.0,2 mM EDTA) was prepared. The IgG solution was combined with agitation with DTT stock at a rate of 20μl of DTT stock per ml of IgG solution. The resultant mixture was allowed to stand at room temperature for 30 minutes without additional mixing (to minimize reoxidation of cysteines to cystines).

Next, the SMCC-Cy7-APC and the reduced IgG were passed over separate PD-10 columns pre-equilibrated with 50 mM MES buffer. For the SMCC-Cy7-APC, most of the color was collected and retained, with steps taken to reduce excessive dilution. For the IgG, eluent was collected in 0.5 ml fractions, with those fractions having peak absorbance at 280 mn being pooled and retained. The concentration of the retained eluents was determined.

The Cy7-APC tandem dye was then promptly coupled to the reduced IgG by reacting the maleimide groups on the Cy7-APC with the free sulfhydryls on the IgG. For coupling, Cy7-APC were coupled with IgG at a rate of 1.5 mg of Cy7-APC per mg of IgG. The reaction tube was wrapped in aluminum foil and rotated for 60 minutes at room temp.

The reaction was stopped by blocking any unreacted free sulfhydryls on the IgG. To stop the reaction, 34/μg (0.34μl) per mg of IgG of a freshly prepared solution of 10 mg N-ethyl maleimide (NEM, MW=125.1)in 0.1 ml dry DMSO was combined with the reaction mixture in the reaction tube, the reaction tube was wrapped with aluminum foil and then rotated for 20 minutes at room temperature.

The resultant product was then dialyzed or exchanged into an appropriate storage buffer(e.g. Tris, NaCl (10 mM Tris, pH 8.2, 150 mM sodium chloride, phix) or PBS (10 mM sodium phosphate, pH 7.0, 150 mM sodium chloride, 1% (w/v) azide).

3. Use of Cy7-APC-CD45RA in Labeling of Cells

Figure 2:
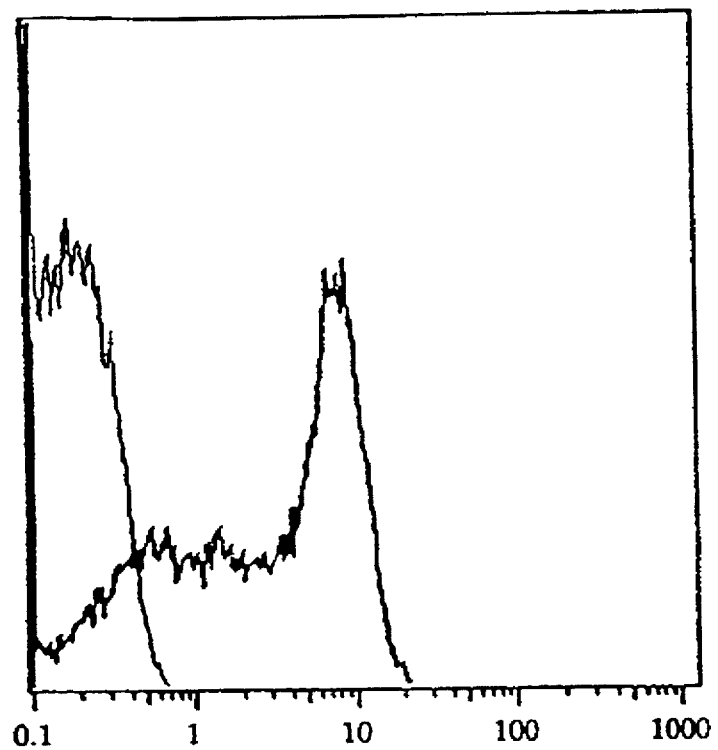
FIG. 2 provides single parameter histograms of unstained cells and cells stained with the label Cy7-APC-CD45RA.

The Cy7-APC-CD45RA conjugate prepared in Example 2 was employed in fluorescence detection assays, as follows. FIG. 2 compares the single parameter histograms obtained with unstained cells (thin line) with that obtained for peripheral blood mononuclear cells (PBMC) stained with Cy7-APC-CD45RA (bold line). The labeled cells are easily separable from unstained, and show the characteristic pattern expected for CD45RA: 60–70% brightly-stained cells, and 30% dim or negatively-stained cells.

Figure 3A:
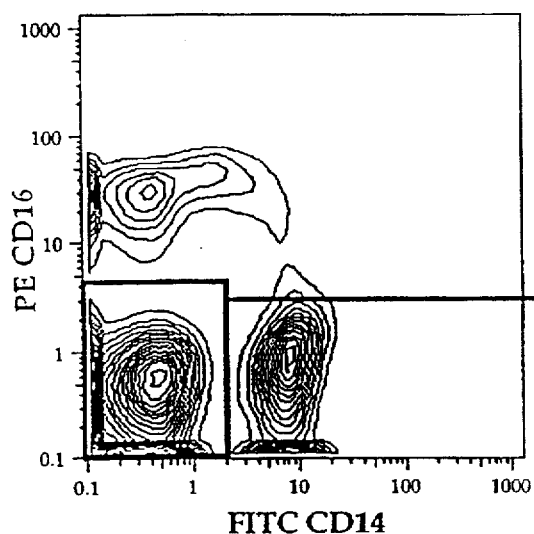
FIGS. 3A–3D demonstrate the use of Cy7-APC-CD45RA in conjunction with six other dye labels in a cell sorting assay.
Figure 3B:
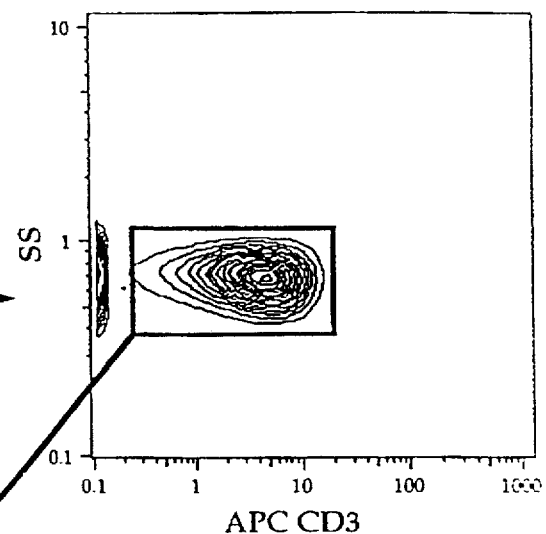
Figure 3C:
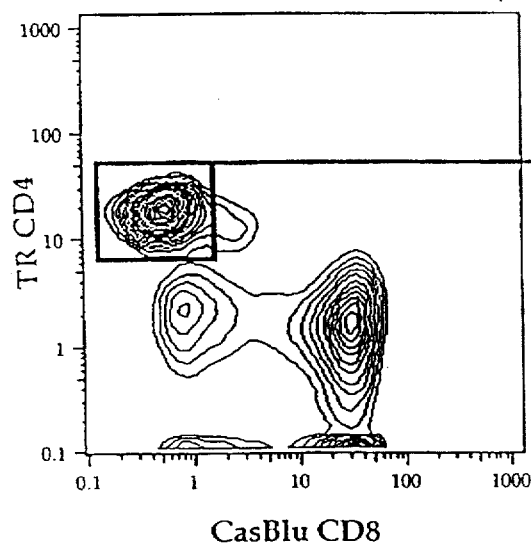
Figure 3D:
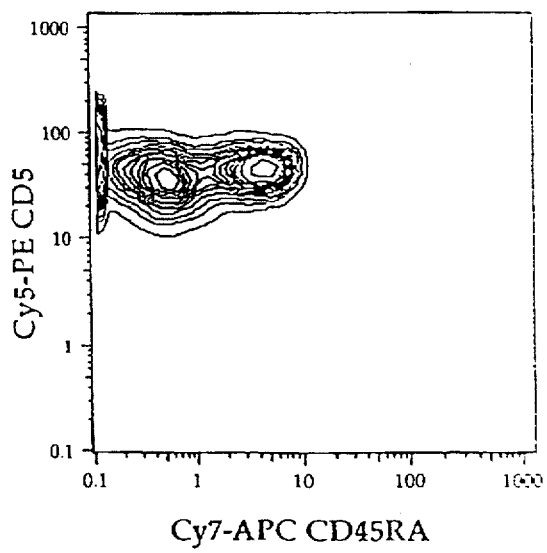

FIGS. 3A–3D demonstrate that Cy7-APC-CD45RA can be used together with at least six other dyes simultaneously in a multiplex assay. PBMC from a healthy adult donor were stained with seven different conjugated monoclonal antibodies: FITC CD14, PE CD16, APC CD3, Cascade Blue CDS, Texas Red CD4, Cy5-PE CD5, and the new Cy7-APC CD45RA. The figures shows successive "gating" to obtain finer and finer subsets of cells, shown in three steps: (i) FIG. 3A shows cells that were negative for CD14 or CD16, lymphocytes, were selected (monocytes and neutrophils stain with CD14 or CD16, respectively); (ii) FIG. 3B shows lymphocytes that are positive for CD3 and are relatively small by side scatter (T cells) were selected (the cells to the left of this box do not stain for CD3 and represent B cells and NK cells); (iii) FIG. 3C shows T cells that are positive for CD4 but not CD8 were selected (these are CD4 T cells). Finally, the right-bottom diagram FIG. 3D shows the distribution of CD5 and CD45RA, the latter revealed by Cy7-APC, on CD4 T cells: as expected, all CD4 T cells are CD5-positive, and about half are CD45RA-positive.

Thus, the Cy7-APC dye represents a novel tandem dye that is useful for flow cytometry (and other fluorescence-based) applications.

It is evident from the above discussion and results that novel conjugates of a Cy7 dye with allophycocyanin useful in fluorescence detection assays are provided. The dyes provide for a readily detectable signal and have excitation spectra compatible with current applications but easily detectable emission spectra which are distinct from other fluorescent probes having similar excitation spectra, being significantly farther to the red. Because of their unique spectral properties including an emission signal that can be readily detected and distinguished from the signals provided by other fluorescent lables, probes comprising the subject dyes can be used in combination with a plurality of fluorescent probes in multi-probe or multiplex assays.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this inventionthat certain changes and modifications may be made thereto without departing from the spirit or scope of the appended claims.

What is claimed is:

1. A tandem dye comprising a conjugate of a Cy7 dye and allophycocyanin.

2. The tandem dye according to claim 1, wherein the number ratio of Cy7 dye to allophycocyanin ranges from 1 to 30.

3. The tandem dye according to claim 1, wherein said Cy7 dye comprises a water solubility enhancing group.

4. The tandem dye according to claim 1, wherein said Cy7 dye is bonded to an amino group of said allophycocyanin.

5. A tandem dye comprising a Cy7 dye covalently bonded to a lysine residue of allophycocyanin, wherein the number ratio of said Cy7 dye to said allophycocyanin ranges from 1 to 30.

6. The dye according to claim 5, wherein said Cy7 dye is selected from the group consisting of Cy7.11-OH, Cy7.12-OH, Cy7.13-OH and Cy7.18-OSU.

7. The dye according to claim 5, wherein said Cy7 dye comprises a water solubility enhancing group.

8. The dye according to claim 7, wherein said Cy7 dye is Cy7.18-OH.

9. A probe for use in fluorescence detection assays comprising a conjugate of a member of a specific binding pair and a tandem dye according to claim 1.

10. The probe according to claim 9, wherein said member of a specific binding pair member is an antibody.

11. The probe according to claim 9, wherein said member of a specific binding pair member is a ligand.

12. The probe according to claim 9, wherein said member of a specific binding pair member is an oligonucleotide.

13. A probe for use in fluorescence detection assays comprising a conjugate of a member of a specific binding pair and a tandem dye according to claim 5, wherein said specific binding pair member is selected from the group consisting of antibodies, haptens and oligonucleotides.

14. In an assay based on fluorescence detection, the improvement comprising:
using the probe according to claim 9 as a label.

15. The assay according to claim 14, wherein said assay is fluorescence activated cell sorting.

16. The assay according to claim 14, wherein said assay is an immunoassay.

17. In a multiplex fluorescence detection assay in which a plurality of fluorescent probes are employed, the improvement comprising:
using as one of said plurality of fluorescent probes the probe according to claim 9.

18. A kit for use in a multiplex fluorescent detection assay comprising a plurality of fluorescent labels, wherein one of said fluorescent labels comprises the tandem dye according to claim 1.

19. The kit according to claim 18, wherein at least one of said plurality of fluorescent labels shares a common excitation spectrum with said tandem dye.

20. The kit according to claim 19, wherein the emission maximum of each said fluorescent labels differs by at least about 15 nm.

* * * * *

UNITED STATES PATENT AND TRADEMARK OFFICE
CERTIFICATE OF CORRECTION

PATENT NO. : 5,714,386

DATED : February 3, 1998

INVENTOR(S) : ROEDERER

It is certified that error appears in the above-indentified patent and that said Letters Patent is hereby corrected as shown below:

Column 3, line 42, delete "we" and insert therefor --are--.

Column 3, line 55, immediately following "amino," insert --formyl,--.

Column 6, line 11, delete "pan" and insert therefor --part--.

Column 6, line 65, delete "NaHCO3" and insert therefor --NaHCO$_3$--.

Column 7, line 2, delete "Cy7obis-OSU" and insert therefor --Cy7-bis-OSU--.

Column 7, line 13, delete "PD-10.9" and insert therefor --PD-10,9--.

Column 7, line 56, delete "prepared immediately" and insert therefor --prepared. Immediately--.

Signed and Sealed this

Fourteenth Day of April, 1998

Attest:

Attesting Officer

BRUCE LEHMAN

Commissioner of Patents and Trademarks